United States Patent
Talley

(10) Patent No.: US 7,211,686 B2
(45) Date of Patent: May 1, 2007

(54) PROCESS FOR MAKING OPTICALLY ACTIVE α-AMINO KETONES AND SELECTED NOVEL OPTICALLY ACTIVE α-AMINO KETONES

(75) Inventor: John J. Talley, Chesterfield, MO (US)

(73) Assignee: Pharmacia Corporation, North Peapack, NJ (US)

( * ) Notice: Subject to any disclaimer, the term of this patent is extended or adjusted under 35 U.S.C. 154(b) by 0 days.

(21) Appl. No.: 11/033,957

(22) Filed: Jan. 12, 2005

(65) Prior Publication Data

US 2005/0187296 A1    Aug. 25, 2005

Related U.S. Application Data

(60) Continuation of application No. 10/366,705, filed on Feb. 14, 2003, now Pat. No. 6,849,756, which is a continuation of application No. 09/973,990, filed on Oct. 11, 2001, now Pat. No. 6,541,654, which is a continuation of application No. 09/611,334, filed on Jul. 5, 2000, now Pat. No. 6,316,656, which is a division of application No. 08/541,767, filed on Oct. 10, 1995, now Pat. No. 6,107,512, which is a division of application No. 08/232,786, filed on Apr. 22, 1994, now Pat. No. 5,488,132, which is a continuation of application No. 07/898,853, filed on Jun. 15, 1992, now Pat. No. 5,364,961.

(51) Int. Cl.
*C07C 229/00* (2006.01)
(52) U.S. Cl. ........................................... 560/39
(58) Field of Classification Search ............... None
See application file for complete search history.

(56) References Cited

U.S. PATENT DOCUMENTS

| | | | |
|---|---|---|---|
| 4,277,420 A | 7/1981 | Koenig | |
| 4,316,847 A | 2/1982 | Batcho et al. | |
| 4,906,773 A | 3/1990 | Taketomi et al. | |
| 4,912,221 A | 3/1990 | O'Reilly et al. | |
| 4,916,252 A | 4/1990 | Sayo et al. | |
| 4,939,288 A | 7/1990 | Talley | |
| 5,086,165 A | 2/1992 | Marshall et al. | |
| 5,364,961 A | 11/1994 | Talley | |
| 5,488,132 A | 1/1996 | Talley | |
| 6,107,512 A * | 8/2000 | Talley | ......................... 560/38 |
| 6,316,656 B1 | 11/2001 | Talley | |
| 6,541,654 B2 | 4/2003 | Talley | |

FOREIGN PATENT DOCUMENTS

| | | |
|---|---|---|
| EP | 375 554 | 6/1990 |
| EP | 409 350 | 1/1991 |
| JP | 3-2152 | 2/1990 |

OTHER PUBLICATIONS

CA 116:129589 (1992).
G. Sholom et al., *Proc. Natl. Acad. Sci.*, USA, 85, 684-688 (1988).
R.G. Almquist et al., *J. Med. Chem.*, 27, 115-120 (1984).
A. Ewenson et al., *J. Med. Chem.*, 29, 295-299 (1986).
A. Ewenson et al., *J. Med. Chem.*, 31, 416-421 (1988).
S. Ouchi et al., *J. Of Antiobiotics*, 1576-1580 (1983).
M. Garcia-Lopez et al., *Tetrahedron Lett.*, 29, 1577-1580 (1988).
R. Meyer et al., *J. Med. Chem.*, 25, 996-999 (1982).
R. Almquist et al., *J. Med. Chem.*, 26, 1292-1299 (1982).
J. McMurray et al., *J. Org. Chem.*, 50, 1112-1115 (1985).
A. Ewenson et al., *Int. J. Peptide Protein Res.*, 31, 269-280 (1988).
R. Almquist et al., *J. Med. Chem.*, 27, 115-120 (1984).
R. Johnson et al., *Int. J. Peptide Protein Res.*, 23, 581-590 (1984).
C. Jennings-White et al., *Tetrahedron Lett.*, 23, 2533-2534 (1982).
M. Holladay et al., *Tet. Lett.*, 24, 4401-4404 (1983).
H. Kagan et al., *J. Am. Chem. Soc.*, 94:18, 6429-6433 (1972).
R. Almquist et al., *J. Med. Chem.*, 23, 1392-1398 (1980).
Holladay, M. et al. Tetrahedron Lett. (1983), 24(41) 4401-4.

* cited by examiner

*Primary Examiner*—Paul A. Zucker
(74) *Attorney, Agent, or Firm*—Banner & Witcoff, Ltd.

(57) ABSTRACT

The invention includes selected novel optically active α-amino ketones which either are themselves useful or are intermediates for the preparation of known ketomethylene pseudopeptides useful as antibiotics, antibiotic enhancers, or enzyme inhibitors. Further, the present invention provides a method for dehydrogenation/asymmetrical hydrogenation to obtain essentially pure antipodes of ketomethylene pseudopeptides having two chiral centers.

7 Claims, No Drawings

PROCESS FOR MAKING OPTICALLY ACTIVE α-AMINO KETONES AND SELECTED NOVEL OPTICALLY ACTIVE α-AMINO KETONES

CROSS REFERENCE TO RELATED APPLICATIONS

This application is a continuation of U.S. patent application Ser. No. 10/366,705, field Feb. 14, 2003, issued as U.S. Pat. No. 6,849,756 B2, which is a continuation of U.S. patent application Ser. No. 09/973,990, filed Oct. 11, 2001, issued as U.S. Pat. No. 6,541,654 B2, which is a continuation of U.S. patent application Ser. No. 09/611,334, filed Jul. 5, 2000, issued as U.S. Pat. No. 6,316,656 B1, which is a divisional of application Ser. No. 08/541,767, filed Oct. 10, 1995, issued as U.S. Pat. No. 6,107,512, which is a divisional of application Ser. No. 08/232,786, filed Apr. 22, 1994, issued as U.S. Pat. No. 5,488,132, which is a continuation of application Ser. No. 07/898,853, filed Jun. 15, 1992, issued as U.S. Pat. No. 5,364,961, each incorporated herein by reference in its entirety.

BACKGROUND OF THE INVENTION

Peptides in which the —CONH— linkage has been replaced by the —COCH$_2$— isosteric moiety are known as ketomethylene pseudopeptides[1] having known utility. For example, such ketomethylene pseudopeptides may be useful as antibiotics, antibiotic enhancers or enzyme inhibitors. Further, this structural modification has been used to make peptide-like molecules with improved metabolic stability.[2] This structural motif has been employed for the preparation of numerous enzyme inhibitors,[3] and has even been found as a natural product.[4] There have been a number of ingenious methods developed for the preparation of this important class of compounds. By far the most common approach to the synthesis of this class of peptide isosteres is to ignore the issue of absolute stereochemistry.[5] There are reports of possible solutions to the question of the absolute configuration of the N-terminal optically active center.[6] There is a singular report of a successful approach to the preparation of ketomethylene pseudopeptides with absolute stereocontrol at both asymmetric centers.[7]

Inhibitor molecules based on the ketomethylene isostere have been found to be potent inhibitors of ACE (angiotensin converting enzyme),[2] Substance P,[3b] carboxypeptidase A,[3c] carboxypeptidase A,[3c] and HIV protease.[8]

The preparation of optically active alpha-amino ketones by dehydrogenation of racemic alpha-amino ketones and hydrogenation using an asymmetric hydrogenation catalyst is disclosed for dehydroketomethylene pseudopeptides having an aromatic substituent adjacent the keto group in U.S. Pat. No. 4,277,420; East German Application Nos. 280,527; 280,528; 280,529; 240,372 described in corresponding Derwent Abstract Numbers 90-362220/49, 90-362221/49, 90-362222/49, 87-057083/09, respectively.

Additional references directed to optically pure optically active intermediates include:
U.S. Pat. No. 4,912,221;
EP Application No. 90307750.1;
U.S. Pat. No. 4,906,773;
U.S. Pat. No. 4,916,252;
U.S. Pat. No. 4,316,847;
EP Application No. 89403599.7;
Japanese Number 3002152A described in WPI Acc No. 91-048825;
German Appl. No. 140-036 described in Derwent Abstract No. 34661C/20.

Disclosure for a rhodium di (1R, 2R)- or (1S, 2S)-bis(phenyl-4-methoxyphenylphosphino)ethane (Rh DiPAMP) catalyst and its use as an enantioselective hydrogenation catalyst is exemplified in each of the following:
J. Am. Chem. Soc. 1977(Aug. 31), 99; 17 pp. 594652;
J. Am. Chem. Soc. 1977(Sep. 6), 94:18 pp. 6429–33;
Synthesis 1979(May) pp. 350–2; and
Chem. Ber. 1981, 114, pp. 1137–49.

The present process takes advantage of the very practical method for the preparation of optically active succinates[9] as a key component for a modified Dakin-West reaction. This protocol effectively introduces the C-terminal optically active center with the appropriate D- or L-amino acid absolute configuration at C-2. The Dakin-West reaction does not however offer a-method for the control of the N-terminal optically active center at C-5. In an effort to control both asymmetric centers of a ketomethylene pseudopeptide, the present invention provides a method for the dehydrogenation/asymmetric hydrogenation of certain ketomethylene pseudopeptides. The invention is a novel synthetic method for the preparation of this class of peptide isostere in which both asymmetric centers are fixed with known absolute configuration. The present method permits the introduction of the C-5 optically active center with very high optical purity. In addition, since the absolute configuration of the C-5 center is induced by the absolute configuration of the asymmetric catalyst ligand, it is possible to make either optical antipode independently by the appropriate choice of ligand absolute configuration.

The flexibility of our synthesis permits the synthesis of very unique analogues of α-amino ketones that have improved biological properties relative to molecules available by more demanding syntheses. The literature is replete with examples of novel amino acid side chains designed to impart improved biological properties to these molecules.

BRIEF SUMMARY OF THE INVENTION

The present invention is a novel compound of the formula (I or I$_1$)

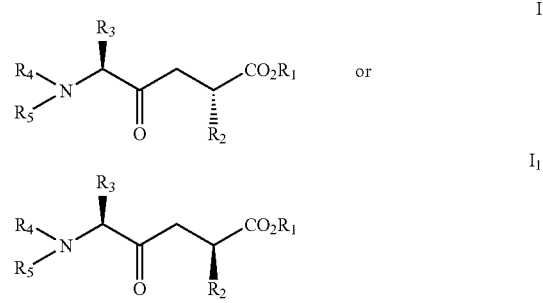

wherein
R$_1$ is hydrogen, alkyl, lower cycloalkyl, or Ar wherein Ar is an aromatic group, preferably CH$_2$Ar, including, particularly, unsubstituted or substituted phenylmethyl;
R$_2$ is CH$_2$R$_9$ wherein R$_9$ is
(a) hydrogen,
(b) C$_1$–C$_4$ alkyl optionally substituted with one or more hydroxyl, C$_1$–C$_3$ alkoxy, chloro, or fluoro, (c) phenyl optionally substituted with one to three of $C_1$–$C_4$ alkyl, halogen where halogen is fluoro, chloro, bromo or iodo, hydroxyl, nitro, $C_1$–$C_3$ alkoxy, or —CO—N($R_7$)$_2$ wherein $R_7$ is, independently, H or $C_1$–$C_4$ alkyl,
(d) a 5–7 member heterocycle such as pyridyl, furyl, indolyl or benzisoxazolyl,
(e) $C_3$–$C_7$ cycloalkyl, or
(f) naphthyl;

$R_3$ is $R_6CH_2$ $R_6$ is
(1) hydrogen;
(2) alkyl of from 1 to 6 carbons optionally substituted by one or two hydroxyl, chloro or fluoro;
(3) cycloalkyl of from 3 to 7 ring carbons;
(4) $Ar_4$ which is a group such as phenyl, or phenyl substituted by one to three substituent(s) consisting of
  (a) alkyl of from one to four carbons,
  (b) halogen consisting of fluoro, chloro, bromo, iodo,
  (c) alkoxy of from one to three carbons,
  (d) nitro,
  (e) amido,
  (f) mono- or di-alkyl (of from one to four carbons) amido, or
  (g) hydroxy;
(5) $Ar_5$ which is tolyl;
(6) $Ar_6$ which is tolyl substituted by one to three substituents consisting of
  (a) alkyl of from of one to four carbons,
  (b) halogen consisting of fluoro, chloro, bromo, iodo,
  (c) alkoxy of from one to three carbons,
  (d) nitro,
  (e) amido,
  (f) mono- or di-alkyl (of from one to four carbons) amido, or
  (g) hydroxy;
(7) $Ar_7$ which is a group optionally attached through a $CH_2$ and is naphthyl or naphthyl substituted by one to three substituents consisting of
  (a) alkyl of from one to four carbons,
  (b) halogen consisting of fluoro, chloro, bromo, iodo,
  (c) alkoxy of from one to three carbons,
  (d) nitro,
  (e) amido,
  (f) mono- or di-alkyl (of from one to four carbons) amido, or
  (g) hydroxy;
(8) $Ar_8$ which is a group such as indol-3-yl, indol-2-yl, or imidazoly-4-yl or indol-3-ylmethyl, indol-2-ylmethyl or imidazol-4-ylmethyl (preferably unsubstituted or substituted phenyl or indol-3-yl);
(9) NHA wherein A is
  (a) trityl,
  (b) hydrogen,
  (c) alkyl of from one to six carbons,
  (d) $R_{10}$ CO wherein $R_{10}$ is (A)hydrogen, (B) alkyl of from one to six carbons optionally substituted with hydroxyl, chloro, or fluoro, (C) phenyl or naphthyl; unsubstituted or substituted with one to three of (i) alkyl of from one to three carbons, (ii) halogen where halogen is F, Cl, Br, or I, (iii) hydroxy, (iv) nitro, (v) alkoxy of from one to three carbons, (vi) CON($R_{11}$)$_2$ wherein $R_{11}$ is independently hydrogen or alkyl of from one to four carbons, or (D) a 5 to 7 member heterocycle such as indolyl, pyridyl, furyl or benzisoxazolyl;
  (e) phthaloyl wherein the aromatic ring is optionally substituted by one to three of (A) alkyl of from one to three carbons, (B) halogen where halogen is F, Cl, Br, or I, (C) hydroxy, (D) nitro, (E) alkoxy of from one to three carbons, (F) CON($R_{11}$)$_2$ wherein $R_{11}$ is independently hydrogen or alkyl of from one to four carbons,
  (f) $R_{12}(R_{13}R_{14}C)_m$CO wherein m is one to three and $R_{12}$, $R_{13}$, and $R_{14}$ are independently (A) hydrogen, (B) chloro or fluoro, (C) alkyl of from one to three carbons optionally substituted by chloro, fluoro, or hydroxy, (D) hydroxy, (E) phenyl or naphthyl optionally substituted by one to three of (i) alkyl of from one to three carbons, (ii) halogen where halogen is F, Cl, Br, or I, (iii) hydroxy, (iv) nitro, (v) alkoxy of from one to three carbons, (vi) CON($R_{11}$)$_2$ wherein $R_{11}$ is independently hydrogen or alkyl of from one to four carbons, (F) alkoxy of from one to three carbons, (G) 5 to 7 member heterocycle such as pyridyl, furyl, or benzisoxazolyl, or (H)$R_{12}$,$R_{13}$, and $R_{14}$ are independently joined to form a monocyclic, bicyclic, or tricycle ring system each ring of which is a cycloalkyl of from three to six carbons, except that only one of $R_{12}$, $R_{13}$ and $R_{14}$ can be hydroxy or alkoxy on the same carbon and can not be hydroxy, chloro or fluoro when m is one;
  (g) $R_{12}(R_{13}$ and $R_{14}C)_m$W wherein m is independently 1 to 3 and W is OCO or $SO_2$ and $R_{12}$, $R_{13}$, and $R_{14}$ are independently as defined above;
  (h) $R_{20}$W wherein $R_{20}$ is a 5 to 7 member heterocycle such as pyridyl, furyl, or benzisoxazolyl;
  (i) $R_{21}$W wherein $R_{21}$ is phenyl or naphthyl unsubstituted or substituted by one to three substituents of (i) alkyl of from one to three carbons, (ii) halogen where halogen is F, Cl, Br, or I, (iii) hydroxy, (iv) nitro, (v) alkoxy of from one to three carbons, (vi) CON($R_{11}$)$_2$ wherein $R_{11}$ is independently hydrogen or alkyl of from one to four carbons;
  (j) $R_{12}(R_{13}R_{14}C)_m$P(O) (O$R_{22}$) wherein $R_{22}$ is alkyl of from one to four carbons or phenyl;
  (k) $R_{20}$P(O)(O$R_{22}$) wherein $R_{22}$ is as defined above;
  (l) $R_{21}$P(O)(O$R_{22}$) wherein $R_{22}$ is as defined above; or
  (m) N($R_{11}$)$_2$ wherein $R_{11}$ is independently as defined above;
(10) $R_{12}(R_{13}R_{14}C)_m$V wherein V is O or NH and $R_{12}$, $R_{13}$ and $R_{14}$ are independently as defined above;
(11) N($R_{11}$)$_2$ wherein $R_{11}$ is independently as defined above;
(12) N$R_{15}$N$R_{16}$ wherein $R_{15}$ and $R_{16}$ are joined to form a 4 to 6 membered saturated nitrogen containing heterocycle which is (a) azetidinyl, (b) pyrrolidinyl, (c) piperidinyl, or (d) morpholinyl;
(13) $R_{17}$OCH$_2$O wherein $R_{17}$ is
  (a) alkyl of from one to six carbons,
  (b) $R_{21}$ wherein $R_{21}$ is independently defined as above; or
  (c) CH$_2$Q$_1$ wherein Q$_1$ is phenyl, naphthyl or a 5 to 7 membered heterocycle;
(14) $R_{17}$OCH$_2$CH$_2$OCH$_2$ wherein $R_{17}$ is independently as defined above;
(15) alkynyl of from two to six carbons optionally substituted with $R_{21}$ where in $R_{21}$ is independently as defined above; or

(16) alkenyl of from two to six carbons optionally substituted with $R_{21}$ where in $R_{21}$ is independently as defined above;

$R_4$ is hydrogen, an amino acid radical or a protecting group such as a substituted or unsubstituted acyl; and $R_5$ is independently hydrogen, alkyl, lower cycloalkyl, or an aromatic group, preferably unsubstituted or substituted phenyl.

The present invention is also a process for the treatment of a compound of the formula (II or II$_1$)

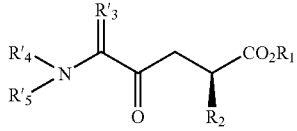

II

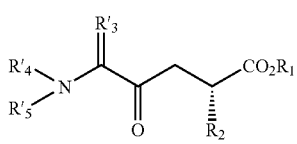

II$_1$ wherein $R_1$ and $R_2$ is as defined above;
$R_3'$ is

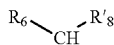 or 

wherein $R_6$ is as defined above; and $R_8'$ is hydrogen, $C_1$–$C_4$ alkyl or cycloalkyl with the proviso that one of $R_6$ or $R_8'$ is hydrogen;

$R_4'$ is a protecting group such as a substituted or unsubstituted acyl or amino acid radical;

$R_5'$ is hydrogen;

with hydrogen in the presence of rhodium (R,R)-(1,2-ethanediyl bis[ortho-methoxyphenyl)phenylphosphine] (H$_2$RhDiPAMP) in deoxygenated solvent;

optionally deprotecting the nitrogen or deprotecting the nitrogen and further treating to add an amino acid radical to the nitrogen to obtain a compound of the formula I or I, wherein $R_1$, $R_2$, $R_3$, $R_4$, $R_5$, and $R_6$ are as defined above.

The present invention is a compound of the formula (II or II$_1$)

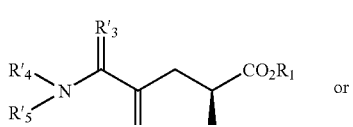

II

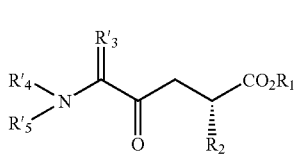

II$_1$ wherein $R_1$, $R_2$, $R_3'$, $R_4'$ and $R_5$ are as defined above.

The present invention is also the preparation of a compound of the formula II or II$_1$ as defined above comprising the treatment of the compound of the formula (III or III$_1$)

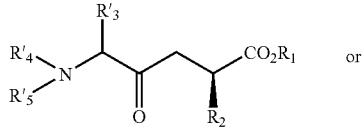

III

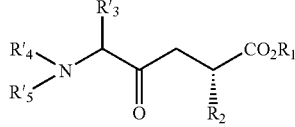

III$_1$ wherein $R_1$, $R_2$, $R_3'$, $R_4'$ and $R_5'$ are as defined above; with tertiary-butyl hypochlorite and 1,4-diazabicyclo[2.2.2]octane (DABCO) to obtain a compound of the formula II or II$_1$.

DETAILED DESCRIPTION OF THE INVENTION $C_1$–$C_3$ or —$C_4$ means alkyl of from one to three or four such as methyl, ethyl, propyl or butyl and isomers thereof and the like.

Protection of the amino group can be accomplished by methods well known to those familiar with amino acid chemistry. For example, the amino group be protected utilizing a carbonyl compound represented by the formula

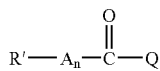

wherein R' represents alkyl radicals having from 1 to about 10 carbon atoms, and aryl, aralkyl and alkaryl radicals having from about 6 to about 26 carbon atoms; or aryl or alkylaryl or aralkyl with suitable carbon numbers, A represents oxygen; n is 0 or 1; and Q represents Cl, Br, I, or C(O)A$_n$R' wherein R', A and n have the same meanings as defined above. Exemplary amino protecting groups are acyl groups including such groups as acetyl, benzoyl, formyl, propionyl, butyryl, toluyl and may include substituted such groups, for example, nitrobenzoyl, and the like. In other words, the amino protecting groups are those commonly used as blocking groups in peptide synthesis.

$C_3$–$C_7$ cycloalkyl means cyclic hydrocarbon groups containing 3 to 7 carbon atoms, such as cyclopropyl, cyclobutyl, cyclopentyl, cyclohexyl, methyl cylopentyl, methyl cyclohexyl, dimethyl cyclopentyl, cycloheptyl and the like.

Ar is an aromatic group which means a phenyl, substituted phenyl, tolyl, substituted tolyl, naphthyl and the like.

Substituted phenyl and substituted tolyl means from one to three substituents such as alkyl, carboxyl, hydroxyl (and base salts thereof), alkoxy, halogen which means fluoro, chloro, bromo, or iodo, $C_2$–$C_4$ acyloxy, aryloxy, aralkoxy, amino, alkyl amido (both mono and di alkylamido), nitro, cyano.

Optically active means the compound includes at least one optically active carbon.

Generally, the process comprising the treatment of the compound of formula II or II$_1$ with hydrogen in the presence of DiPAMP to obtain the compound of the formula I or I$_1$ respectively is as set out hereinafter. The reaction is accomplished at from about 1 to 100 psig and at a temperature from about 0° C. to 60° C. preferably at about room temperature and at a pressure about 40 psig, in inert solvents such as methanol, ethanol, tetrahydrofuran, dichloromethane, acetonitrile and the like or mixtures thereof.

Evaluation of the results may be accomplished by standard methods, such as vapor phase chromatography on a optically active capillary column, or by HPLC (high performance liquid chromatography) on a optically active column or by evaluation of the optical rotation of a solution of the compound.

A Fisher-Porter bottle is charged with the appropriate substrate dissolved in deoxygenated methanol along with 0.1–1.0 mol percent rhodium (R, R)-DiPAMP (R,R)-(1,2-ethanediyl bis[(o-methoxyphenyl)phenylphosphine]. After 5 nitrogen purges (40 psig) the solution was purged 5 times with hydrogen (40 psig) and then allowed to hydrogenate at room temperature for 1–24 h. The hydrogen is replaced with nitrogen and the contents of the bottle concentrated in vacuo. The catalyst residue is separated from the optically active ketomethylene pseudopeptides I or I$_1$ by dissolving the product in iso-octane. The catalyst residue is not soluble in iso-octane.

A general procedure for the hydrolysis of optically active N,O-protected ketomethylene pseudopeptides of the formula I or I$_1$ wherein R$_4$' is a protecting group is as follows. A sample of the optically active N,O-protected ketomethylene pseudopeptide derivative is refluxed for 24 h with 12 N hydrochloric acid. The solvent is removed in vacuo. The residue is taken up in water and re-concentrated in vacuo. After thoroughly drying under vacuum the hydrochloride salt is converted to the free amine by treatment with excess propylene oxide. The precipitated amino acid is then isolated by filtration and optionally recrystallized from water/methanol.

An evaluation is made of optical purity by optically active vapor phase chromatography. The N,O-protected optically active ketomethylene pseudopeptide derivatives are analyzed by optically active gas chromatography for optical purity. A solution of the racemic ketomethylene pseudopeptide derivative in dichloromethane is separated into the two enantiomers by a 25 meter Chirasil Val III capillary column with flame ionization detection. After conditions for separation of the two enantiomers are established, each optically active hydrogenation product is evaluated for the extent of optical purity.

Generally, the compound of the formula II or II$_1$ are prepared by the method shown in Scheme 2 hereinafter.

Scheme 2

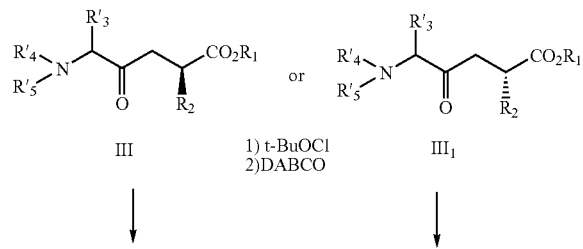

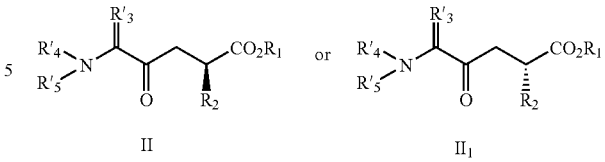

The conditions of the treatment of formula III or III$_1$ by tertiary-butyl hypochlorite are at a temperature of 0° C.–50° C. in an inert solvent such as dichloromethane, chloroform, acetonitrile and the like The product of this treatment is then further treated with 1,4-diazabicyclo[2.2.2]octane (DABCO) at a temperature of 0° C.–50° C. in an inert solvent such as dichloromethane, tetrahydrofuran, chloroform, acetonitrile and the like.

Compounds of the formula III or III$_1$ are prepared by methods known in the art or by methods analogous to those known in the art from starting material which are known or which can be prepared by known methods.

Variations in these conditions and evaluations for different compounds within the definitions of the formula I or I$_1$ are within the skill of an ordinarily skilled artisan.

The general procedure for removal of a protecting group, such as the tert-butyl ester is as follows. A sample of the product, I and I$_1$, is dissolved in dichloromethane and treated with an equal (volume) amount of trifluoroacetic acid at 0° C. The solution is allowed to warm to room temperature and the progress of the reaction monitored by TLC. When the reaction is finished the solvents are removed in vacuo and the residue purified by crystallization or flash chromatography on silica gel.

The compounds of the Formula I or I$_1$ are useful as intermediates in the preparation of pharmacologically active compounds. It is contemplated that certain intermediates disclosed herein will manifest similar activity.

The compounds of Formula I or I$_1$ which manifest pharmacologically active are useful both in the free base and the free acid form or in the form of base salts thereof, as well as, in the form of acid addition salts. All forms are within the scope of the invention. In practice, use of the salt form amounts to use of the free acid or free base form. Appropriate pharmaceutically acceptable salts within the scope of the invention are those derived from mineral and organic acids or those derived from bases such as suitable organic and inorganic bases. For example, see "Pharmaceutical Salts", *J. Pharm. Sci.*, 66(1), 1–19 (1977). The acid addition salts of said compounds are prepared either by dissolving the free base of compound I or I$_1$ in aqueous or aqueous alcohol solution or other suitable solvents containing the appropriate acid or base and isolating the salt by evaporating the solution, or by reacting the free base of Compound I or I$_1$ with an acid as well as reacting compound I or I$_1$ having an acid group thereon with a base such that the reactions are in an organic solvent, in which case the salt separates directly or can be obtained by concentration of the solution.

The base salts of compounds of Formula I or I$_1$ described above are prepared by reacting the appropriate base with a stoichiometric equivalent of the acid compounds of Formula I or I$_1$ to obtain pharmacologically acceptable base salts thereof.

Contemplated equivalents of the general formulas set forth above for the compounds I or I$_1$ as well as the compounds useful to prepare compounds I or I$_1$ are compounds otherwise corresponding thereto and having the same general properties wherein one or more of the various R groups are simple variations of the substituents as defined therein, e.g., wherein $R_2$ or $R_3$ is a higher alkyl group. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Part 1. Preparation of 2(R), 5(S)N-acetyl-Phe[COCH$_2$]Ala-OMe

Step 1. Cyclodehydration of N-benzoyl D,L-phenylalanine with acetic anhydride: General method for the preparation of alpha-amino acid oxazolones. A 100 mL round bottomed flask is charged with N-benzoyl D,L-phenylalanine (6.75 g, 25.1 mmol) and 50 mL of acetic anhydride. The contents of the flask are warmed to 100 C. for 1 h and then the excess acetic anhydride is removed in vacuo. The oily residue thus produced is taken up in boiling hexanes, filtered, and allowed to stand undisturbed whereupon white crystals of pure product forms which are isolated by filtration and further dried in vacuo to give 4.48 g, 71% of pure oxazolone, mp 70–71 C.

Step 2. Preparation of N-acetyl 2(R), 5(R,S)-Phe[COCH$_2$] Ala-OMe; methyl (R,S)-N-acetyl-2(R)-methyl-4-keto-6-phenyl hexanoate.

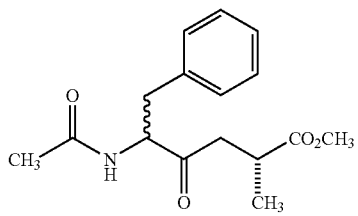

A 250 mL round-bottomed flask was charged with N-acetyl-D,L-phenylalanine oxazolone (9.40 g, 72.5 mmol), 2-methyl mono-methylsuccinate (10.68 g, 73.2 mmol) and 50 mL of chloroform. The solution was treated with 4-dimethylaminopyridine (1.00 g, 8.18 mmol), and triethylamine (7.80 g, 77.2 mmol) and then stirred at room temperature for 72 h. The solution was concentrated in vacuo and the residue dissolved in ethyl acetate, the solution was washed with 3N HCl, sat. aq. NaHCO$_3$, brine, dried over anhyd. MgSO$_4$, filtered and concentrated to give an orange oil. This crude product was purified by chromatography on a Waters Prep-500 instrument over 2 silica gel cartridges eluting with hexanes/ethyl acetate. The appropriate fractions were combined and concentrated to give the desired ketomethylene as a 1:1 mixture of diastereomers at C-5, 8.20 g, 40.8%.

Step 3. Preparation of methyl 5-N-acetylamino)-2(R)-methyl-4-oxo-6-phenyl-hexenoate.

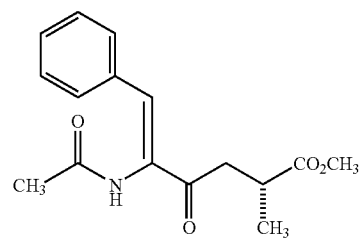

A 25 mL one-necked round-bottomed flask was equipped with a magnetic stir bar, nitrogen inlet, and reflux condenser was charged with methyl 5(R,S)-N-acetylamino)-2-(R)-methyl-4-oxo-6-phenyl hexanoate (200 mg, 0.88 mmol) and 13 mL of chloroform. To this solution was added tert-butyl hypochlorite (250 mg, 2.90 mmol) via syringe. The solution was stirred at room temperature for 5 minutes and then the progress of the reaction evaluated by thin layer chromatography (TLC) on silica gel eluting with 1:1 hexane:ethyl acetate, the starting material had $R_f$=0.32 and the N-chloro intermediate had an $R_f$=0.84. After 1.5 h the reaction was complete and the solution was then concentrated in vacuo and redissolved in the minimum amount of benzene. The benzene solution of the N-chloro intermediate was then added to a solution of 1,4-diazabicyclo[2.2.2]octane (330 mg, 2.95 mmol) in 20 mL of benzene. This solution was stirred at room temperature for 1.5 h and then evaluated by TLC on silica gel eluting with 1:1 hexane:ethyl acetate which showed that the starting material was gone and the desired product had been formed, $R_f$=0.40. The solution was diluted with ethyl acetate and poured into a separatory funnel and washed with 3N HCl, sat. aq. NaHCO$_3$, brine, dried over anhyd. MgSO$_4$, filtered and concentrated to give methyl 5-(acetylamino)-2(R)-methyl-4-oxo-6-phenyl-hex-5-enoate as an oil, which was used directly in the next step.

Step 4. Asymmetric hydrogenation of methyl N-acetyl-2 (R)-methyl-4-keto-6-phenyl hex-5-eneoate: Preparation of methyl 5(S)-N-acetyl-2(R)-methyl-4-keto-6-phenyl hexanoate.

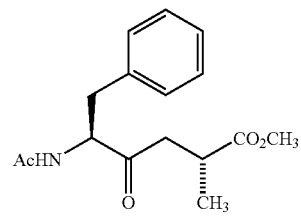

A Fisher-Porter bottle was charged with 30 mL of degassed methanol and the crude product from Step 2 along with rhodium (R,R)-DiPAMP (15 mg, 0.02 mmol). The solution was flushed 5 times with nitrogen and 5 times with hydrogen and hydrogenated at 40 psig for 24 h. The bottle was opened and the solution concentrated in vacuo to give the crude product which was separated from the catalyst by radial chromatography on silica gel eluting with 20% ethyl acetate in hexane to give 170 mg, 85% of methyl 5(S)-N-acetyl-2(R)-methyl-4-keto-6-phenyl hexanoate, TLC on silica gel eluting with 1:1 hexane:ethyl acetate $R_f$=0.33, $^1$H and $^{13}$C nmr showed that only one diastereomer was present.

Part II. Verification of the Absolute Configuration.

Step 5. Acidic hydrolysis of methyl 5(R,S)-N-acetyl-2(R)-methyl-4-keto-6-phenyl hexanoate: Preparation of 5(S)-N-amino-2(R)-methyl-4-keto-6-phenyl hexanoic acid hydrochloride.

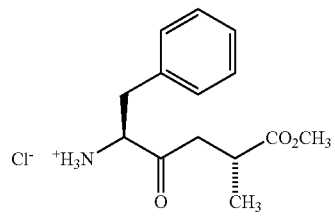

A 100 mL round-bottomed flask equipped with a reflux condenser was charged with methyl 5(R,S)-N-acetyl-2(R)-methyl-4-keto-6-phenyl hexanoate (4.15 g, 15 mmol), 30 mL of conc. HCl, and 15 mL of glacial acetic acid. The solution was warmed to 95° C. for 16 h, then cooled to room temperature washed 2 times with ether and the aqueous phase concentrated in vacuo to give 3.90 g, of a white powder, 96%. The crude product was then dissolved in acetonitrile, however some material did not dissolve. The insoluble material, 650 mg, was examined by $^1$H and $^{13}$C nmr which showed that it was a single diastereomer, mp 162–164° C. dec.

Step 2. Preparation of 5(S)-N-(1,1-dimethylethoxycarbonylamino)-2(R)-methyl-4-keto-6-phenyl hexanoic acid from 5(S)-amino-2(R)-methyl-4-keto-6-phenyl hexanoic acid hydrochloride.

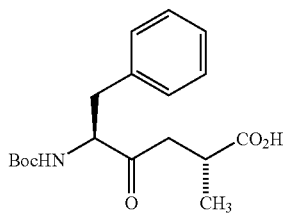

A portion of this pure diastereomer (200 mg, 0.74 mmol) was placed in a 50 mL Erlenmeyer flask and diluted with 10 mL of dioxane and 10 mL of 0.1N NaOH. The above solution was then treated with a solution of di-tert-butylpyrocarbonate (185 mg, 0.85 mmol) in 2 mL of dioxane. The pH of the solution was maintained at 8.5 by the periodic addition of 0.1N NaOH. When the pH stabilized, ca. 2 h, the pH of the solution was adjusted to 3.0 by the addition of 1N KHSO$_4$ and then extracted 4 times with ethyl acetate. The combined ethyl acetate extracts were washed with brine, dried over anhyd. MgSO$_4$, filtered and concentrated in vacuo to give a white crystalline solid. This material was then recrystallized from hexane ethyl acetate to give pure 5(S)-N-(1,1-dimethylethoxycarbonylamino)-2(R)-methyl-4-keto-6-phenyl hexanoic acid, mp 126.0–127.5° C., 162 mg, 69%. These crystals were suitable for single crystal X-ray crystallography which confirmed that the absolute configuration was 2(R), 5(S).

Step 3. Preparation of methyl 5(S)-N-acetyl-2(R)-methyl-4-keto-6-phenyl hexanoate.

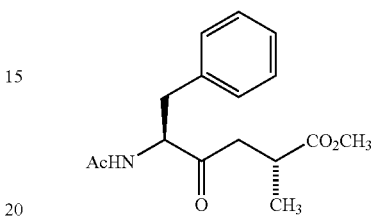

A sample of the single diastereomer from Step 1 was converted to methyl 5(S)-N-acetyl-2(R)-methyl-4-keto-6-phenyl hexanoate by acetylation with acetic anhydride followed by esterification with methyl iodide and 1,8-diazabicyclo[5.4.0]undec-7-ene (DBU). The material prepared in this manner was identical to the material prepared in Part 1, Step 3, confirming the 2(R),5(S) absolute configuration of the material prepared in Part 1, Step 3.

REFERENCES AND NOTES

[1] Spatola, A. F., *Chemistry and Biochemistry Amino Acids, Peptides, and Proteins*. Weinstein, B.; Marcel Dekker, New York, 1983, pp 267–357.

[2] Almquist, R. G.; Olsen, C. M.; Uyeno, E. T.; Toll, L. J. *Med. Chem.*, 1984, 27, 115.

[3] (a) Almquist, R. G., Chao, W. R.; Ellis, M. E.; Handsom, H. L. *J. Med. Chem.*, 1980, 23, 1392, (b) Ewenson, A.; Laufer, R.; Chorev, M.; Selinger, Z.; Gilom, C., *J. Med. Chem.*, 1986, 29, 295, (c) Shohom, G.; Christianson, W.; Oren, D. A. *Proc. Natl. Acad. Sci. USA*, 1988, 85, 684, (d) Ewenson, A.; Laufer, R.; Chorev, M.; Selinger, Z.; Gilom, C. *J. Med. Chem.*, 1988, 31, 416.

[4] Ohuchi, S.; Suda, H.; Naganawa, H.; Takita, T.; Aoyagi, T.; Umezawa, H.; Nakamura, H.; Litaka, Y., *J. Antibiot.*, 1983, 36, 1576.

[5] (a) Garcia-Lopez, M. T.; Gonzalez-Muniz, R.; Harto, J. R. *Tetrahedron Lett.*, 1988, 29, 1577, (b) Meyer, R. F.; Essemburg, A. D.; Smith, R. D.; Kaplan, H. R. *J. Med. Chem.*, 1982, 25, 996, (c) Almquist, R. G.; Crase, J.; Jennings-White, C.; Meyer, R. F.; Hoefle, M. L.; Smith, R. D.; Essenburg, A. D.; Kaplan, H. R. *J. Med. Chem.*, 1982, 25, 1292, (d) McMurray, J. S.; Dyckes, D. F. *J. Org. Chem.*, 1985, 50, 1112, (e) Ewenson, A.; Cohen-Suissa, R.; Levian-Teitelbaum, D.; Selinger, Zl; Chorev, M.; Gilon, C. *Int. J., Peptide Protein Res.*, 1988, 31, 269, (f) Almquist, R. G.; Olsen, C. M.; Uyeno, E. T.; Toll, L. J. *Med. Chem.*, 1984, 24, 115.

[6] (a) Johnson, R. L.; Miller, R. B. *Int. J. Peptide Protein Res.*, 1984, 23, 581, (b) Jennings-White, C.; Almquist, R. G. *Tetrahedron Lett.*, 1982, 23, 2533.

[7] Holladay, M.; Rich, D. H. *Tetrahedron Lett.*, 1983, 24, 4401.

[8] Marshall, G. R. Washington University, St. Louis, Mo. has incorporated certain ketomethylene pseudopeptides into inhibitors of HIV-1 protease of U.S. Pat. No. 5,086,165, Feb. 2, 1992. Some of these key optically active intermediates were supplied by the inventor.
[9] Talley, J. J. U.S. Pat. No. 4,939,288, Jul. 3, 1990.

The invention claimed is:

1. An essentially pure optically active diastereomer of the formula (I or $I_1$)

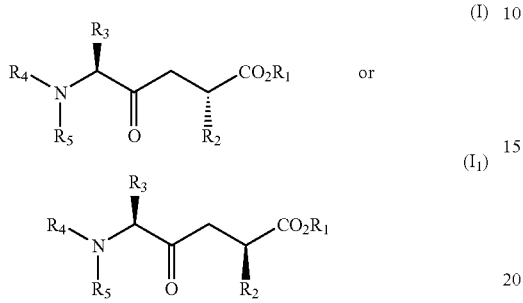

or a pharmaceutically acceptable salt thereof;
wherein
$R_1$ is a hydrogen radical, an alkyl radical, a lower cycloalkyl radical, or an aromatic radical;
$R_2$ is $CH_2R_9$ wherein $R_9$ is
 (a) a hydrogen radical;
 (b) an alkyl radical having one to four carbon atoms optionally substituted with one or more radical selected from the group consisting of hydroxyl, alkoxy having one to three carbon atoms, chloro, and fluoro;
 (c) a phenyl radical optionally substituted with one to three radical selected from the group consisting of alkyl having one to four carbon atoms, fluoro, chloro, bromo, iodo, hydroxyl, nitro, alkoxy having one to three carbon atoms, and —CO—N($R_7$)$_2$, wherein each $R_7$ is, independently a hydrogen radical or an alkyl radical having one to four carbon atoms;
 (d) a five to seven member heterocyclic radical;
 (e) a cycloalkyl radical having three to seven ring members; or
 (f) a naphthyl radical;
$R_3$ is
—$CH_2R_6$ wherein $R_6$ is
 (1) a hydrogen radical;
 (2) an alkyl radical having one to six carbon atoms optionally substituted with one or two radical selected from the group consisting of hydroxyl, chloro, and fluoro;
 (3) a cycloalkyl radical having three to seven ring members;
 (4) a phenyl radical optionally substituted with one to three radical selected from the group consisting of
  (a) alkyl radical having one to four carbon atoms,
  (b) a fluoro, chloro, bromo, or iodo radical,
  (c) an alkoxy radical having one to three carbon atoms,
  (d) a nitro radical,
  (e) an amido radical,
  (f) an amido radical substituted with one or two alkyl groups having one to four carbon atoms, and
  (g) a hydroxy radical;
 (5) a tolyl radical;
 (6) a tolyl radical substituted with one to three radical selected from the group consisting of
  (a) an alkyl radical having one to four carbon atoms,
  (b) a fluoro, chloro, bromo, or iodo radical,
  (c) an alkoxy radical having one to three carbon atoms,
  (d) a nitro radical,
  (e) an amido radical,
  (f) an amido radical substituted with one or two alkyl groups having one to four carbon atoms, and
  (g) a hydroxy radical;
 (7) a naphthyl radical optionally substituted with one to three radical selected from the group consisting of
  (a) an alkyl radical having one to four carbon atoms,
  (b) a fluoro, chloro, bromo, or iodo radical,
  (d) an alkoxy radical having one to three carbon atoms,
  (d) a nitro radical,
  (e) an amido radical,
  (f) an amido radical substituted with one or two alkyl groups having one to four carbon atoms, and
  (g) a hydroxy radical;
 (8) an indol-3-yl, indol-2-yl, imidazoly-4-yl, indol-3-ylmethyl, indol-2-ylmethyl or imidazol-4-ylmethyl radical;
 (9) a radical of the formula NHA wherein A is
  (a) a trityl radical,
  (b) a hydrogen radical,
  (c) an alkyl radical having one to six carbon atoms,
  (d) a radical of the formula $R_{10}CO$ wherein $R_{10}$ is
   (A) a hydrogen radical, (B) an alkyl radical having one to six carbon atoms and optionally substituted with one or more hydroxyl, chloro, or fluoro radicals, (C) a phenyl or a naphthyl radical, each of witch is optionally substituted with one to three radicals selected from group consisting of (i) an alkyl radical having one to three carbon atoms, (ii) a fluoro, chloro, bromo or iodo radical, (iii) a hydroxy, radical, (iv) a nitro radical, (v) an alkoxy radical having one to three carbon atoms, and (vi) a radical of the formula CON($R_{11}$)$_2$ wherein each $R_{11}$ is independently a hydrogen radical or an alkyl radical having one to four carbon atoms, or (D) a five to seven member heterocyclic radical;
  (e) a phthaloyl radical, optionally substituted at its aromatic ring with one to three radicals selected from the group consisting of (A) an alkyl radical having to three carbon atoms, (B) a fluoro, chloro, bromo or iodo radical, (C) a hydroxy radical, (D) a nitro radical, (E) an alkoxy radical having one to three carbon atoms, and (F) a radical of the formula CON($R_{11}$)$_2$ wherein each $R_{11}$ is independently a hydrogen radical or an alkyl radical having one to four carbon atoms,
  (f) a radical of the formula $R_{12}(R_{13}R_{14}C)_mCO$, wherein m is one to three and $R_{12}$, $R_{13}$, and $R_{14}$ are each independently selected from the group consisting of (A) a hydrogen radical, (B) a chloro or fluoro radical, (C) an alkyl radical having one to three carbon atoms and optionally substituted with one or more chloro, fluoro, or hydroxy radicals, (D) a hydroxy radical, (E) a phenyl or naphthyl radical, each of witch may be optionally substituted with one to three radicals selected from the group consisting of (i) an alkyl radical having one to three carbon atoms, (ii) a fluoro, chloro, bromo, or iodo radical, (iii) a hydroxy radical, (iv) a nitro radical, (v) an alkoxy radical having one to three carbon atoms, and (vi) a radical of the formula $CON(R_{11})_2$ wherein each $R_{11}$ is independently a hydrogen radical or an alkyl radical having one to four carbon atoms, (F) an alkoxy radical having one to three carbon atoms, and (G) a five to seven member heterocyclic radical, or wherein $R_{12}$, $R_{13}$, and $R_{14}$ are joined to form a monocyclic, bicyclic, or tricyclic ring system, each ring of which is a cycloalkyl radical having three to six carbon atoms, except that only one of $R_{12}$, $R_{13}$, and $R_{14}$ is hydroxy or alkoxy on the same carbon atom and $R_{12}$, $R_{13}$, and $R_{14}$ are not hydroxy, chloro, or fluoro when m is one;

(g) a radical of the formula $R_{12}(R_{13}R_{14}C)_mW$, wherein m is one to three and W is OCO or $SO_2$ and $R_{12}$, $R_{13}$, and $R_{14}$ are as defined above;

(h) a radical of the formula $R_{20}W$ wherein $R_{20}$ is a five to seven member heterocyclic radical;

(i) a radical of the formula $R_{21}W$ wherein $R_{21}$ is a phenyl or a naphthyl radical, each of which is optionally substituted with one to three radicals selected from the group consisting of (i) an alkyl radical having one to three carbon atoms, (ii) a fluoro, chloro, bromo, or iodo radical, (iii) a hydroxy radical, (iv) a nitro radical, (v) an alkoxy radical having one to three carbon atoms, and (vi) a radical of the formula $CON(R_{11})_2$ wherein each $R_{11}$ is independently a hydrogen radical or an alkyl radical having one to four carbon atoms;

(j) a radical of the formula $R_{12}(R_{13}R_{14}C)_mP(O)(OR_{22})$, wherein $R_{22}$ is an alkyl radical having one to four carbon atoms or phenyl and $R_{12}$, $R_{13}$, and $R_{14}$ are as defines above;

(k) a radical of the formula $R_{20}P(O)(OR_{22})$, wherein $R_{20}$ and $R_{22}$ are as defined above; or (l) a radical of the formula $R_{21}P(O)(OR_{22})$, wherein $R_{21}$ and $R_{22}$ are as defined above;

(10) a radical of the formula $R_{12}(R_{13}R_{14}C)_mV$, wherein V is O or NH and $R_{12}$, $R_{13}$, and $R_{14}$ are as defined above;

(11) a radical of the formula $N(R_{11})_2$, wherein each $R_{11}$ is independently as defined above;

(12) a radical of the formula $NR_{15}NR_{16}$, wherein $R_{15}$ and $R_{16}$ are joined to form an azetidinyl, a pyrrolidinyl, a piperidinyl, or a morpholinyl radical;

(13) a radical of the formula $R_{17}OCH_2O$ wherein $R_{17}$ is
 (a) an alkyl radical having one to six carbon atoms,
 (b) a radical of the formula $R_{21}$ as defined above; or
 (c) a radical of the formula $CH_2Q_1$ wherein $Q_1$ is a phenyl radical or a naphthyl radical or a five to seven member heterocyclic radical;

(14) a radical of the formula $R_{17}OCH_2CH_2OCH_2$ wherein $R_{17}$ is as defined above;

(15) an alkynyl radical having two to six carbon atoms and optionally substituted with a radical of the formula $R_{21}$ as defined above; or

(16) an alkenyl radical having two to six carbon atoms and optionally substituted with a radical of the formula $R_{21}$ as defined above;

$R_4$ is hydrogen, an amino acid radical or a protecting group;

$R_5$ is a hydrogen radical.

2. The diastereomer of claim 1, wherein, in said diastereomer or said pharmaceutically acceptable salt thereof, $R_4$ is an alkoxycarbonyl, a phenoxycarbonyl, a naphthyloxycarbonyl, a phenylalkoxycarbonyl, a napththylalkoxycarbonyl, an alkanoyl, a formly, a phenylalkanoyl, a napthylalkanoyl, a benzoyl, or a naphthoyl radical, wherein each alkyl group of $R_4$ is from one to ten carbon atoms and wherein each phenyl or naphthyl group of $R_4$ is optionally substituted at one more carbon atoms with an alkyl radical.

3. The diastereomer of claim 1, wherein
in said diastereomer or said pharmaceutically acceptable salt thereof, $R_6$ is a phenyl radical optionally substituted with one to three radicals selected from the group consisting of
 (a) an alkyl radical having one to four carbon atoms,
 (b) a fluoro, chloro, bromo, or iodo radical,
 (e) an alkoxy radical having one to three carbon atoms,
 (d) a nitro radical,
 (e) an amido radical,
 (f) an amido radical substituted with one or two alkyl groups having one to four carbon atoms, and
 (g) a hydroxy radical.

4. The diastereomer of claim 3, wherein
in said diastereomer or said pharmaceutically acceptable salt thereof, $R_3$ is phenylmethyl and $R_2$ is methyl.

5. The diastereomer of claim 3, wherein
in said diastereomer or said pharmaceutically acceptable salt thereof, $R_4$ is $COCH_3$.

6. The diastereomer of claim 3, wherein
in said diastereomer or said pharmaceutically acceptable salt thereof, $R_6$ is methyl and $R_2$ is phenylmethyl.

7. The diastereomer of claim 3, wherein
in said diastereomer or said pharmaceutically acceptable salt thereof, $R_6$ in naphthyl.

* * * * *

UNITED STATES PATENT AND TRADEMARK OFFICE
CERTIFICATE OF CORRECTION

PATENT NO. : 7,211,686 B2  Page 1 of 1
APPLICATION NO. : 11/033957
DATED : May 1, 2007
INVENTOR(S) : John J. Talley It is certified that error appears in the above-identified patent and that said Letters Patent is hereby corrected as shown below:

In Claim 1, Column 13, Lines 30, 35, 49, 55, and 66:
  Please delete "radical" and insert --radicals--

In Claim 1, Column 14, Line 11:
  Please delete "radical" and insert --radicals--

In Claim 1, Column 14, Line 21:
  Please delete "imidazoly" and insert --imidazol--

In Claim 1, Column 14, Line 33 and 61:
  Please delete "witch" and insert --which--

In Claim 1, Column 14, Line 37:
  Please delete "hydroxy, radical," and insert --hydroxy radical,--

In Claim 1, Column 15, Line 32:
  Please delete "defines" and insert --defined--

In Claim 2, Column 16, Line 17:
  Please delete "formly" and insert --formyl--

Signed and Sealed this

Thirteenth Day of November, 2007

JON W. DUDAS
*Director of the United States Patent and Trademark Office*